United States Patent [19]
Ehlinger

[11] Patent Number: 5,418,166
[45] Date of Patent: May 23, 1995

[54] PROCESS AND DEVICE FOR THE BIOLOGICAL TREATMENT OF EFFLUENTS FROM WINE CELLARS

[75] Inventor: Frédéric Ehlinger, Le Peco, France

[73] Assignee: Societe Degremont, Rueil Malmaison, France

[21] Appl. No.: 43,869

[22] Filed: Apr. 7, 1993

[30] Foreign Application Priority Data

Apr. 7, 1992 [FR] France .................. 92 04247

[51] Int. Cl.⁶ .................................... C12S 13/00
[52] U.S. Cl. .................. 435/262; 435/255.1; 210/620
[58] Field of Search ............ 435/161, 162, 255, 262, 435/274, 275, 313, 314, 264, 315, 316, 813, 88, 255.1, 255.2; 426/11, 16, 31; 210/610, 620, 614

[56] References Cited

U.S. PATENT DOCUMENTS

| | | |
|---|---|---|
| 2,121,458 | 6/1938 | Vogelbusch . |
| 2,802,774 | 8/1957 | Griesbach ............. 435/315 |
| 3,274,075 | 9/1966 | Kersting . |
| 3,400,051 | 9/1968 | Hofschneider ............. 435/315 |
| 3,751,388 | 8/1973 | Tabana et al. . |
| 4,035,517 | 7/1977 | Magny et al. ............. 426/31 |
| 4,183,807 | 1/1980 | Yoshizawa et al. ........... 210/610 |
| 5,075,008 | 12/1991 | Chigusa et al. ............. 210/610 |

FOREIGN PATENT DOCUMENTS

| | | |
|---|---|---|
| 423404 | 4/1991 | European Pat. Off. . |
| 1156344 | 5/1958 | France . |
| 2176927 | 11/1973 | France . |
| 2354967 | 1/1978 | France . |

Primary Examiner—William H. Beisner
Attorney, Agent, or Firm—Pollock, Vande Sande & Priddy

[57] ABSTRACT

Process for the biological treatment of effluents from wine cellars by transferring the yeasts contained in the effluents to a medium into which oxygen or air is continuously supplied so that these yeasts, placed under aerobic conditions, consume the carbon substrates of these effluents in which they develop, thus ensuring the treatment thereof.

4 Claims, 1 Drawing Sheet

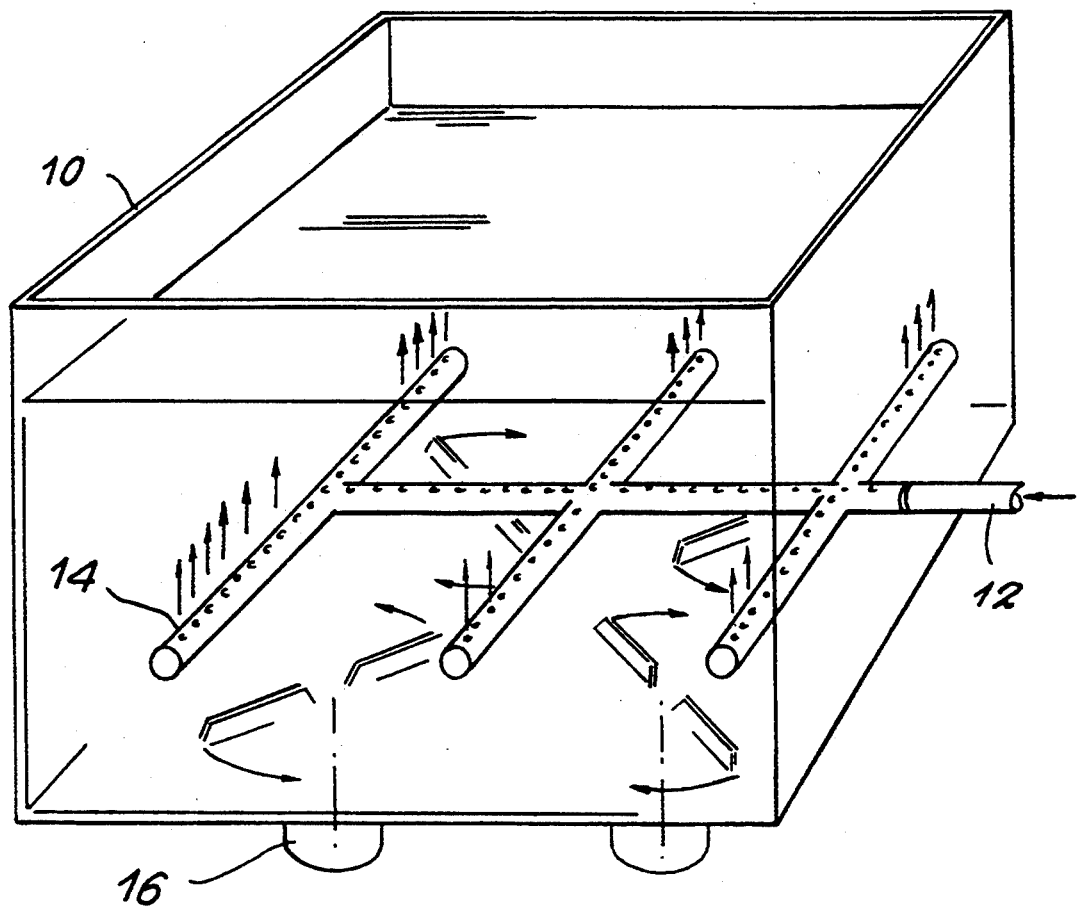

PROCESS AND DEVICE FOR THE BIOLOGICAL TREATMENT OF EFFLUENTS FROM WINE CELLARS

FIELD OF THE INVENTION

The present invention relates to the biological treatment of effluents from wine cellars.

BACKGROUND OF THE INVENTION

The use of yeasts whose metabolism is generally employed for the purpose of manufacturing high value-added molecules such as ethanol, flavors, short and long-chain fatty acids is well known in the field of biotechnology. These processes are known as anaerobic fermentation.

Furthermore, it is known that when these yeasts are placed under aerobic conditions, they modify their metabolism. The substrate carbon is then used only for the production of biomass. Yeasts "breathe", that is to say they produce water and carbon dioxide, while multiplying. In the publication "Water Science and Technology", Vol. 19, RIO page 11-21, 1987, Huyard et al. showed that the aerobic metabolism of yeasts could be used to remove the carbon pollution from waste water. However, to this end, it is necessary to select pure yeast strains or collection strains, cultivate them in a fermenter so as to produce a yeast sediment and then to inoculate with this yeast sediment the effluent which it is desired to depollute. However, the success of this operation depends on the adaptation of these pure strains to the substrate. Now, the latter is often very heterogeneous, that is to say it consists of a multiplicity of molecules. The result is that, because most of the yeasts used are not adapted to this substrate, the period of acclimation or adaptation of these yeast strains to the substrate is thereby all the longer and more unpredictable.

In the effluents from wine cellars, which are obtained for example by the discharge of the lees from wine vats, there are many yeasts which are especially adapted to the substrates obtained from the processing of grape musts. In these lees, the yeasts are maintained under anaerobic conditions.

BRIEF DESCRIPTION OF THE INVENTION

The invention proposes to use these yeasts under aerobic conditions so as to remove the pollution caused by effluents from wine cellars.

To this end, the invention provides a process for the biological treatment of effluents from wine cellars in which the process essentially consists in transferring the yeasts contained in the effluents to a medium into which oxygen or air is continuously supplied so that the yeasts, placed under aerobic conditions, immediately begin to consume the carbon substrates of these effluents in which they develop, thus ensuring the treatment thereof.

Thus, as is evident, the use according to the invention of the said yeasts for this biological treatment does not require any specific inoculation or period of adaptation or acclimation of the yeasts to the substrates.

The invention also relates to a device for implementing the process specified above, which essentially comprises a reactor consisting of a tank equipped with means for the diffusion of oxygen or air in the form of fine bubbles, it being possible, in addition, for this tank to be provided with mechanical stirring means, positioned at the bottom of the tank so as to eliminate any dead space.

According to the invention, the pH of the medium is regulated at a value less than 3.5 so as to limit the development of bacteria.

BRIEF DESCRIPTION OF THE FIGURES

The sole FIGURE of the attached drawing represents very schematically, by way of example, and in perspective, an embodiment of a reactor for implementing the invention.

DETAILED DESCRIPTION OF THE INVENTION

This reactor is therefore provided in the form of a tank 10 into which a conduit 12 for feeding air or oxygen under pressure opens, this conduit supplying a plurality of diffusers such as 14, consisting for example of pipes equipped with diffusers or nozzles for introducing air or oxygen in the form of fine bubbles into the mass of effluent to be treated which is contained in the tank 10. The latter comprises, in addition, bottom stirrers 16 ensuring an efficient mixing of the effluent in order to eliminate any dead space.

As specified above, the yeasts contained in the effluent are thus placed under aerobic conditions and they consume the carbon substrates of these effluents so as to ensure the treatment thereof. Provision is made to regulate the pH of the effluent mass at a value less than 3.5 so as to limit the development of the bacteria.

In order to make clear the technical effects and advantages conveyed by this invention, comparative test results have been given as a non limitative example.

Purification tests have been carried out on an effluent resulting from a wine settling vat with an overall DCO of 40 g/l and a soluble DCO of 10 g/l.

The two purifying techniques were compared: on the one hand, the aerobic purification by yeasts and on the other the traditional activated sludge. The same effluent received applied voluminal loads, expressed in Kg of soluble DCO/m3 per day that were very different.

From the very beginning of the experiment and throughout all the tests, the "activated sludge" pilot plant voluminal load remained very low, around 1.5 Kg DCO/m3 per day, with poor waste disposal performances (lower than 50%).

On the other hand, the initial load in the yeast purification pilot plant was initially set at 3 kg of soluble DCO/m3 per day and increased to reach 20 kg DCO/m3 per day after 15 days, with a very good purifying output (in the order of 90%).

These results clearly demonstrate the vast superiority of the purifying process according to the invention when compared to traditional methods.

I claim:

1. A process for the biological treatment of effluent from wine cellars, containing uncultivated, naturally occurring yeasts from wine fermentation, comprising the steps:
    containing the effluent, and the uncultivated yeasts therein, in a treatment tank;
    subjecting the effluent to continuous aeration for maintaining aerobic conditions for the yeasts;
    regulating a pH of the effluent at less than 3.5;
    wherein the aerobically conditioned yeasts consume carbonaceous substrates of the effluent.

2. A process for the biological treatment of effluent from wine cellars as set forth in claim 1 wherein the aeration is accomplished by continuously diffusing bubbles into the effluent.

3. A process for the biological treatment of effluent from wine cellars as set forth in claim 2 further comprising the step of stirring the effluent.

4. A process for the biological treatment of effluent from wine cellars as set forth in claim 1 further comprising the step of stirring the effluent.

* * * * *